(12) United States Patent
Lange

(10) Patent No.: US 8,308,778 B2
(45) Date of Patent: Nov. 13, 2012

(54) LONGITUDINAL IMPLANT

(75) Inventor: Robert Lange, Paris (FR)

(73) Assignee: CO-Ligne AG, Paris (FR)

( * ) Notice: Subject to any disclaimer, the term of this patent is extended or adjusted under 35 U.S.C. 154(b) by 84 days.

(21) Appl. No.: 12/605,899

(22) Filed: Oct. 26, 2009

(65) Prior Publication Data

US 2010/0042163 A1 Feb. 18, 2010

Related U.S. Application Data

(63) Continuation of application No. 10/506,803, filed as application No. PCT/CH02/00136 on Mar. 6, 2002, now abandoned.

(30) Foreign Application Priority Data

Mar. 9, 2001 (EP) .................................. 01810243

(51) Int. Cl.
A61B 17/80 (2006.01)
(52) U.S. Cl. .......................... 606/298; 606/284; 606/285
(58) Field of Classification Search .................. 606/255, 606/261, 264–265, 292, 298, 284–285
See application file for complete search history.

(56) References Cited

U.S. PATENT DOCUMENTS

| 4,403,606 | A | 9/1983 | Woo et al. |
|---|---|---|---|
| 4,590,928 | A | 5/1986 | Hunt et al. |
| 4,696,290 | A | 9/1987 | Steffee |
| 4,743,260 | A | 5/1988 | Burton |
| 5,084,051 | A | 1/1992 | Tormala et al. |
| 5,129,899 | A | 7/1992 | Small et al. |
| 5,294,391 | A | 3/1994 | McMillin |
| 5,556,687 | A | 9/1996 | McMillin |
| 5,584,887 | A | 12/1996 | Kambin |
| 6,280,445 | B1 | 8/2001 | Morrison et al. |
| 6,342,055 | B1 | 1/2002 | Eisermann et al. |
| 2002/0123750 | A1 | 9/2002 | Eisermann et al. |

FOREIGN PATENT DOCUMENTS

| DE | 39 14 164 C | 1/1991 |
|---|---|---|
| EP | 0 637 437 A | 2/1995 |
| FR | 2 555 902 A | 6/1985 |
| WO | 9007304 A | 7/1990 |
| WO | 9709000 A | 3/1997 |

Primary Examiner — Alvin Stewart
Assistant Examiner — Julianna N Harvey
(74) Attorney, Agent, or Firm — Sughrue Mion, PLLC

(57) ABSTRACT

The longitudinal implant is fastened to bones on either side of a damaged area through a connecting device. Said implant is comprised of a filament or fiber composite material and said connecting device is made of a material harder than said longitudinal implant. The longitudinal implant is preferably made of a carbon filament composite material, wherein the filament are encapsulated in a polymer matrix.

9 Claims, 3 Drawing Sheets

FIG. 1
FIG. 2
FIG. 3
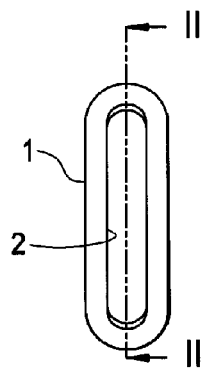
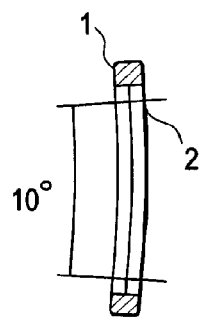
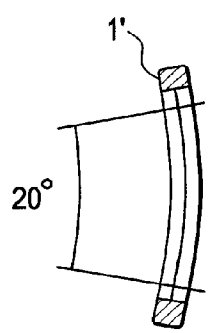
FIG. 4
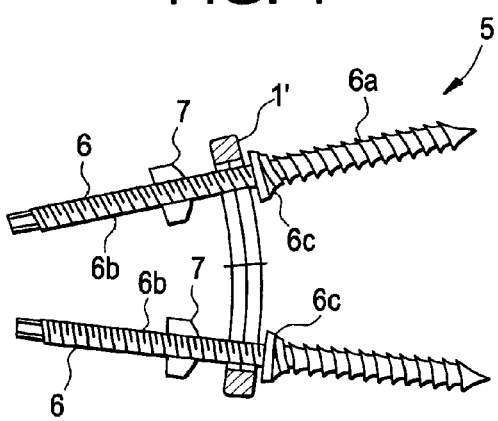
FIG. 5
FIG. 6
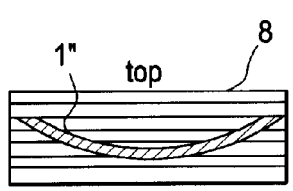
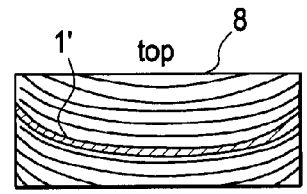

LONGITUDINAL IMPLANT

CROSS REFERENCE TO RELATED APPLICATIONS

This is a Continuation of U.S. application Ser. No. 10/506,803 filed Sep. 7, 2004, which is a §371 National Stage Application of PCT/CH02/00136 filed Mar. 6, 2002; the entire disclosure of the prior applications are considered part of the disclosure of the accompanying Continuation Application and are hereby incorporated by reference.

This invention relates to a longitudinal implant and connecting device wherein said longitudinal implant is fastened to bones on either side of a damaged area through said connecting device.

In some spinal repair situations, the damaged area of the spine is spanned by a slotted plate through which pedicle screws are inserted and fastened to the pedicle bones on either side of a damaged area. This fixes the spatial distance between the pedicle bones and therefore fixes the distance between vertebrae so that the damaged area of the spine can be repaired. In other spinal situations, the damaged area of the spine is spanned by a rod. At least two connectors are slidable along the rod connecting pedicle screws or hooks to the rod. Such a rod and fixation system is disclosed in EP 0 923 908A (Robert Lange).

Spinal repair is often times accomplished with hollow cages in which bone fragments are inserted that will grow to an extent to fuse the upper and lower vertebrae together at the damaged area. By fixing and holding the distance between these vertebrae, the bone in the cages will have time to grow and join the vertebrae together.

It is an objective of this invention to provide an elongated implant and pedicle screw or hook fixation system providing an increased stability.

The implant of the device according to this invention is comprised of a filament composite material—and said pedicle screws or hooks are made of a material harder than said implant. The implant provides a surface that has more friction than a titanium implant. If the implant is a plate having a longitudinal slot, the plate is placed between a nut and an upper surface of a pedicle screw. The plate can be squeezed and locked into position because of the squeezing and the increased friction between titanium and the filament composite material. When all members are titanium, the required position is not always available and indentations are often provided along the slot.

Fixation systems manufactured from metals such as titanium alloy and stainless steel confound postoperative radiologic assessments because they are radiopac and can produce artifact. The use of an implant comprised of a fiber reinforced polymer composite permits better diagnostic assessment of soft tissue and bone by normal radiographic methods.

According to a preferred embodiment of the invention, the fibers are aligned lengthwise, so that compression will not change their strength characteristics to any extent even when compressed. Preferably the fibers or filaments are oriented to resist biomechanical forces.

Other advantages and features of the present invention will be apparent to those skilled in this art reaching the following specification with reference to the accompanying drawings in which:

FIG. 1 is a view of an embodiment of an implant of this invention;

FIG. 2 is a section along line I-I of FIG. 1;

FIG. 3 is a section through an embodiment of the implant with a different curvature;

FIG. 4 shows the implant according to FIG. 3 connecting two pedicle screws;

Figure 7:
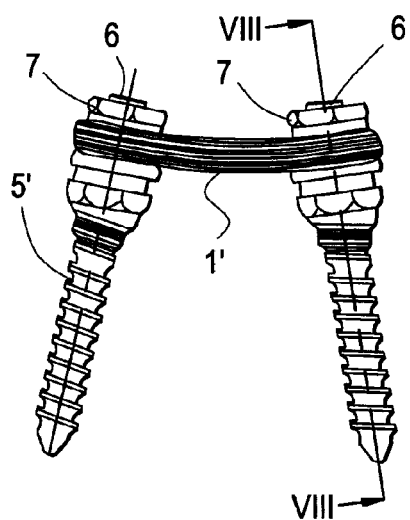
Figure 8:
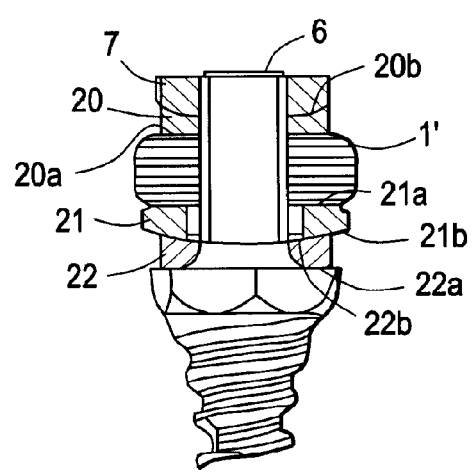
Figure 9:
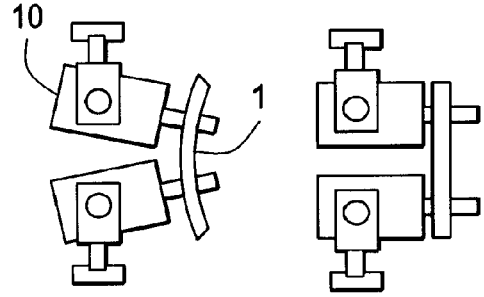
Figure 10:
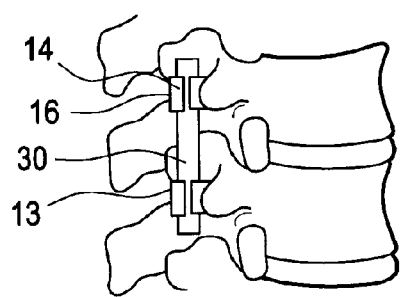
Figure 11:
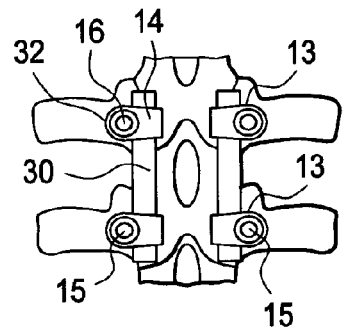
Figure 12:
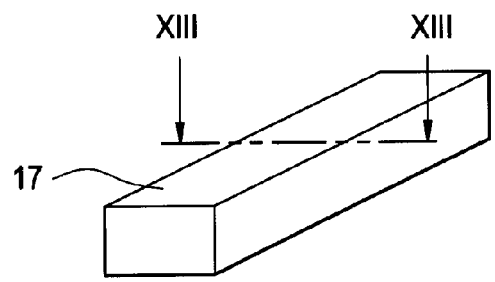
Figure 13:
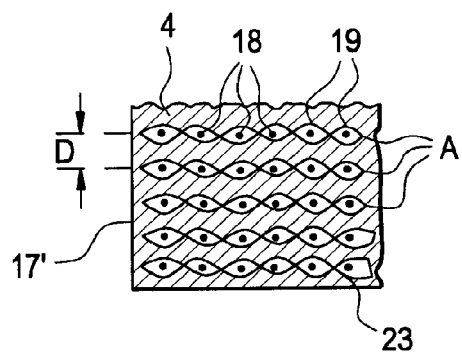

FIG. 5 a schematic view of a material block with horizontal fiber and an implant machined from this block;

FIG. 6 a schematic view of a material block with a curvature fiber orientation and an implant machined from this block;

FIG. 7 a side view of a connecting device of this invention;

FIG. 8 a partial section through the connecting device;

FIG. 9 a side view of an implant testing configuration;

FIGS. 10 and 11 overall views showing rods or rails connecting two vertebrae of a spinal cord;

FIG. 12 a perspective view of another embodiment of an implant of this invention and FIG. 13 a section along line XIII-XIII of FIG. 12.

FIGS. 1 and 2 disclose a plate 1 having a longitudinal slot 2 extending along a substantial portion of its length. The plate has a curvature of about 100 as shown in FIG. 2. FIG. 3 discloses a plate 1' which has a curvature of 20°.

The plates 1 and 1' as well as rods 30 and rails 17 are manufactured from a composite material composed of long filaments or fibers 18 and 19 encapsulated in a matrix 4 as shown in FIG. 13. The filaments or fibers 18 and 19 are preferably long carbon filaments and the matrix is preferably a polymer. Preferably the carbon filaments or fibers 18 and 19 are encapsulated in the polymer polyether-ketoneetherketoneketone (PEMKK). PEKEKK is a known biocompatible polymer. Another possible polymer is polyetheretherketone (PEEK). PFKEKK is preferred to PEEK because of its greater physical and chemical resistance properties. These characteristics impart greater stability to the plates 1 and 1', rods 30 and rails 17 or other connecting parts during a long-term implantation.

FIGS. 4, 7 and 8 disclose a pedical plate fixation systems 5 and 5' comprising a plate 1', two bone screws 6 and two nuts 7. The screws 6 and the nuts 7 are manufactured from steel or medical grade titanium alloy. Bone screws 6 are common in the orthopedic arts. The screws 6 are provided with bone engaging threads 6a and at its other end a screw segment 6b with a conventional thread. The thread 6a flairs outwardly to an enlarged portion 6c. The enlarged portions 6c have a width greater than the width of the slot 2. The screw segment 6b extends outwardly from the enlarged portion 6c and extends through the slot 2. The nut 7 is received by the screw segment 6b, and since the slot 2 is manufactured without any additional recesses or indentations, bevels or slants (see FIGS. 1, 2, 3, 4, 7 and 8) the plate 1' can be grasped between the enlarged portion 6c and the nut 7 to tightly secure the plate 1 by threading the nut 7 toward the enlarged portion 6c.

The embodiment according to FIG. 7 is provided with slip washers 20, 21 and 22 having a planar surface 20a, 21a, 22a and a concave or convex surface 20b, 21b, 22b. The planar surfaces 20a and 21a are touching the plate 1' are preferably provided with rips (not shown), which are depressed in the plate 1' and which prevent the screw 6 from moving along the slot 2.

As the carbon-filament composition material of the plate 1 is softer than titanium and at its surface is somewhat rougher than a titanium surface, the plate 1 can be squeezed between the enlarged portion 6c and the nut 7. This prevents the screws 6 from moving along the slot 2 both by depression caused by the squeezing and the enhanced friction there between.

The filaments 3 encapsulated in the polymer matrix 4 are oriented as shown in FIGS. 7 and B. The plate 1 is machined from a block 8 having a curvature fiber orientation as indicated in FIG. 6. The curvature of the fiber lay-up is the same as the curvature of the plate 1 or plate 2. The filaments 3 in the matrix 4 are therefore aligned lengthwise of the slot 2. The FIG. 5 shows a block 8' with a parallel curvature lay-up and the in the plate 1' machined from this block 8' the filaments do not follow the curvature of the plate 11 and are shorter. With the testing configuration 10 disclosed in FIG. 9, tests were conducted using the ASTM provisional standard for spinal implants. This mechanical testing has shown that the strength of the plate 1 and 1' is similar to plates made from stainless steel and titanium. The goal of stabilization has not been sacrificed. As material of the plates 1 and 1' is radiolucent, the plates do not interfere with diagnostic methods.

As already mentioned, the implant according to this invention can also be a rod 12 as disclosed in FIGS. 10 and 11 ox a rail according to FIGS. 12 and 13. Two connectors 13 include two clamping members 14 connecting pedicle screws 15 to said rods 12. The rods 12 and rails are made from the same material as the plates 1 and 1' and the filaments encapsulated in the matrix are preferably oriented in an axial direction. A rail 17 with a rectangular cross section as shown in FIGS. 12 and 13 is more stable to rotation than a rod.

Another advantage of implants manufactured from a carbon filament composite material is that its strength, flexibility and hardness can be varied by changing the ratio of filaments to plastic. It has been found, that "bone growth" is enhanced when it is under a certain degree of physiological stress. Thus, it will be desirable to select a composite ratio for the plate to gain the required degree of stiffness without sacrificing any strength. The ratio of filaments to plastic is preferably higher than 40% (weight) and more preferably higher than 60% (weight).

The filaments of fibers are not randomly embedded, but oriented in layers A as shown in FIG. A. The layers A can be parallel to each other and to a surface 23 as shown in FIG. 13. The layers A may be made up of woven filaments 18 and 19. The filaments 18 are oriented in the axial direction of the longitudinal implant 1, 17 and 30. The filaments 19 are oriented perpendicular to the axial direction. The filaments 18 and 19 are oriented to resist the biomechanical forces as for example bending force as shown in FIG. 9. The filaments can also be coiled to resist torsion forces. The distance D between two layers A is preferably less than 0.5 mm and preferably about 0.1 mm.

What is claimed is:

1. A longitudinal implant and connecting device wherein said longitudinal implant is fastenable to bones on either side of a damaged area through said connecting device, said implant and connecting device comprising:

a longitudinal implant made of a filament or fiber composite material, wherein filaments or fibers in said material are oriented to resist biomechanical forces, and
   a connecting device made of a material harder than said longitudinal implant,
   wherein, said connecting device is operative to squeeze and lock the longitudinal implant into position both by depression caused by a squeezing and increased friction between the harder material of the connecting device and the composite material of the longitudinal implant, and wherein the implant is one of an elongated structure, the structure having a longitudinal slot extending along a substantial portion of its length and wherein filaments or fibers are aligned lengthwise, so that compression will not change their strength characteristics to any extent even when compressed, and
   wherein the implant is formed without any recesses, bevels, or slants, adjacent to the longitudinal slot.

2. The longitudinal implant and connecting device according to claim 1, wherein the longitudinal implant is made of a carbon filament composite material.

3. The longitudinal implant and connecting device according to claim 1 or 2, wherein the filaments are encapsulated in a polymer matrix.

4. The longitudinal implant and connecting device according to claim 3, wherein the filaments are encapsulated in PEEK or PEKEKK.

5. The longitudinal implant and connecting device according to claim 1, wherein the connecting device comprising a pedicle screw having an upper section having a width greater than the width of said slot and an exteriorly threaded portion extending outwardly from said section and extending through said slot.

6. The longitudinal implant and connecting device according to claim 5, wherein an interiorally threaded nut is received by an outer end of said threaded portion whereby said implant can be grasped between said upper section and said nut to tightly secure said plate by threading said upper section.

7. The longitudinal implant and connecting device according to claim 1, wherein said connecting device comprises a screw and a nut, each of which is made of titanium.

8. The longitudinal implant and connecting device according to claim 1, wherein said implant is a plate.

9. The longitudinal implant and connecting device according to claim 1 or 2, wherein the filaments are woven, comprising first filaments that are oriented in the axial direction of the implant, and second filaments that are oriented perpendicular to the axial direction of the implant.

* * * * *

UNITED STATES PATENT AND TRADEMARK OFFICE
CERTIFICATE OF CORRECTION

| | |
|---|---|
| PATENT NO. | : 8,308,778 B2 |
| APPLICATION NO. | : 12/605899 |
| DATED | : November 13, 2012 |
| INVENTOR(S) | : Robert Lange |

It is certified that error appears in the above-identified patent and that said Letters Patent is hereby corrected as shown below:

On the Title Page, item (73) Assignee should read as follows: CO-Ligne AG, ~~Paris (FR)~~

<u>Zurich (CH)</u>

Signed and Sealed this
Twenty-first Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,308,778 B2
APPLICATION NO.    : 12/605899
DATED              : November 13, 2012
INVENTOR(S)        : Robert Lange It is certified that error appears in the above-identified patent and that said Letters Patent is hereby corrected as shown below:

This certificate supersedes the Certificate of Correction issued October 21, 2014. The certificate which issued on October 21, 2014 is vacated because petition to correct assignee under 3.81(b) (filed on August 29, 2014) was not granted by the Office of Petitions. The Certificate of Correction which issued on October 21, 2014 was published in error and should not have been issued for this patent. The assignee is reinstated on the title page of patent at Item (73) as --CO-Ligne AG, Paris(FR)--.

Signed and Sealed this
Fourteenth Day of April, 2015

Michelle K. Lee
*Director of the United States Patent and Trademark Office*